United States Patent [19]

Rieber et al.

[11] Patent Number: 4,512,795
[45] Date of Patent: Apr. 23, 1985

[54] NORBORNANE COMPOUNDS, PLANT GROWTH REGULATORS CONTAINING THESE COMPOUNDS, AND THEIR INTERMEDIATES

[75] Inventors: Norbert Rieber; Rolf Platz, both of Mannheim; Johann Jung, Limburgerhof, all of Fed. Rep. of Germany

[73] Assignee: BASF Aktiengesellschaft, Fed. Rep. of Germany

[21] Appl. No.: 457,172

[22] Filed: Jan. 11, 1983

[30] Foreign Application Priority Data

Jan. 16, 1982 [DE] Fed. Rep. of Germany ....... 3201190
Mar. 6, 1982 [DE] Fed. Rep. of Germany ....... 3208090
Mar. 6, 1982 [DE] Fed. Rep. of Germany ....... 3208091

[51] Int. Cl.³ .................... A01N 43/62; A01N 43/64; C07D 229/02; C07D 249/16
[52] U.S. Cl. ........................................ 71/88; 71/92; 548/259; 260/239 E
[58] Field of Search .................... 260/239 AR, 239 E; 548/259; 71/88, 92

[56] References Cited

U.S. PATENT DOCUMENTS 4,189,434 2/1980 Platz et al. ............... 260/239 E
4,259,235 3/1981 Platz et al. ............... 260/239 E

OTHER PUBLICATIONS

Gassman et al., *Journal of the American Chemical Society*, 90, (1968), pp. 7276–7282.
Jung et al., Chem. Abstracts 93:180846g, (1980).
Rieber et al., Chem. Abstracts 95:7117p, (1981).
Rademacher et al., Chem. Abstracts 96:117420k, (1982).

*Primary Examiner*—Donald G. Daus
*Assistant Examiner*—William A. Teoli, Jr.
*Attorney, Agent, or Firm*—Keil & Weinkauf

[57] ABSTRACT

Diazatricyclononene compounds of the formula

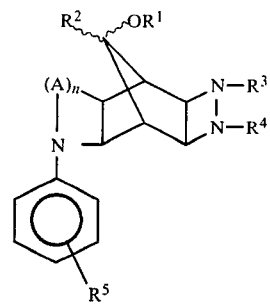

and their intermediates, i.e. norbornane compounds of the formula

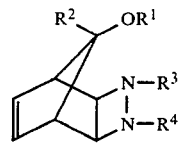

where $R^1$, $R^2$, $R^3$, $R^4$, $R^5$, A and n have the meanings given in the claims and in the description, their preparation and their use as plant protection agents or plant growth regulators.

3 Claims, No Drawings

NORBORNANE COMPOUNDS, PLANT GROWTH REGULATORS CONTAINING THESE COMPOUNDS, AND THEIR INTERMEDIATES

The present invention relates to novel tetracyclic nitrogen-containing norbornane derivatives, plant growth regulators containing these compounds, and their novel intermediates.

It has been disclosed that polycyclic nitrogen-containing norbornane compounds, eg. 5-(4-chloro(or 4-bromo)phenyl)-3,4,5,9,10-pentaazatetracyclo[5,4,1,0$^{2,6}$,0$^{8,11}$]dodeca-3,9-diene, may be used for regulating plant growth (German Laid-Open Applications DOS No. 2,615,878 and DOS No. 2,742,034).

Compounds of the type

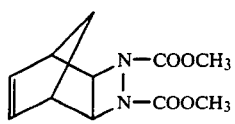

(cf. J.Amer.Chem.Soc., 91 (1969), 5668) and their use as starting materials for the preparation of plant protection agents (German Laid-Open Applications DOS No. 2,165,878 and DOS No. 2,742,034) are also known from the literature.

We have found that the novel compounds of the formula II -

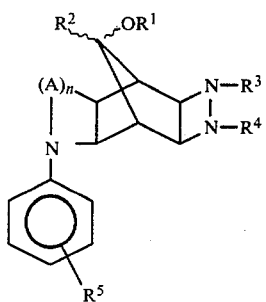

where A is $-N=N-$, n is 0 or 1, $R^1$ is hydrogen, an acyclic or cyclic alkyl or alkylcarbonyl radical (for example, where alkyl is of 1 to 5 carbon atoms), trimethylsilyl or trifluoroacetyl, $R^2$ is hydrogen, or $R^1$ and $R^2$ together constitute a bond, $R^3$ and $R^4$ are identical or different and are each hydrogen or alkoxycarbonyl (for example, of 1 to 4 carbon atoms), or together constitute a bond, and $R^5$ is hydrogen, halogen or haloalkyl (for example, of 1 to 4 carbon atoms), and the steric arrangement of substituents $OR^1$ and $R^2$ at the $C_1$ bridge is not defined, are useful for regulating plant growth.

The novel compounds can be prepared by the processes of which general descriptions are given in German Laid-Open Applications DOS No. 2,615,878, DOS No. 2,742,034 and DOS No. 3,001,580. Examples of suitable methods are:

1. The reaction of a compound I, where $R^1$, $R^2$, $R^3$ and $R^4$ have the above meanings, with an aryl azide, where $R^5$ has the above meanings, to give a triazoline derivative (n=1).

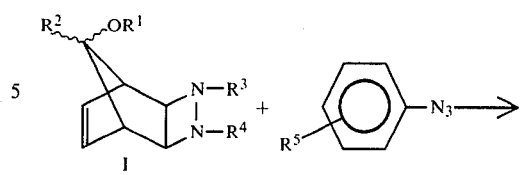

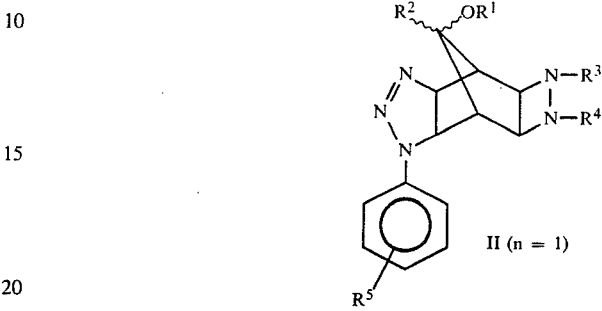

2. Elimination of $N_2$ from the resulting triazoline derivatives in the presence of an acid to give the corresponding aziridine derivative (n=0).

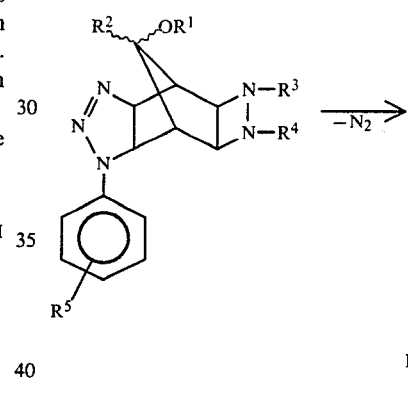

3. Hydrolysis and decarboxylation of the triazoline or aziridine derivative, wherein $R^3$ and $R^4$ are each —COOalkyl, with aqueous or alcoholic caustic alkali solution to give the corresponding hydrazine derivative wherein $R^3$ and $R^4$ are each H, and oxidation of the latter, with or without prior isolation, with aqueous NaOCl or $H_2O_2$ solution to give the azo compound in which $R^3$ and $R^4$ constitute a bond.

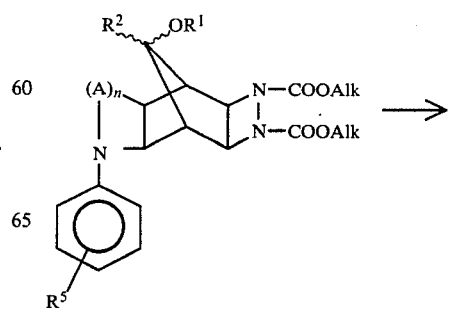

-continued

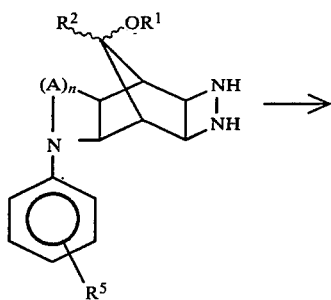

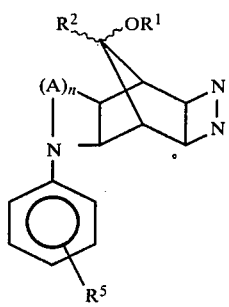

The corresponding reaction of an ester compound of the formula II, where n is 0 or 1, $R^1$ is alkylcarbonyl, $R^2$ is H, and $R^3$ and $R^4$ are each —COOAlk, gives the corresponding hydrazine or azo derivative in which $R^1$ and $R^2$ are each H.

The reaction of a compound I with an aryl azide to give a triazoline derivative II (n=1) is carried out, for example, using stoichiometric or non-stoichiometric amounts of the starting materials, in the presence or absence of a solvent, at not more than 140° C., preferably from 20° to 100° C. The choice of solvent depends on the solubility of the starting materials. The products either are precipitated on cooling or, where a polar solvent is used, by the addition of a non-polar solvent, or can be obtained by evaporating down the solution.

The elimination of nitrogen from the triazoline derivative to give the aziridine derivative can be effected, for example in a solvent, by adding an acid. In most cases, it is sufficient to add a catalytic amount of, for example, sulfuric acid, acetic acid or trifluoroacetic acid, at not more than 120° C., preferably from 20° to 80° C.

The hydrolysis and decarboxylation of the triazoline or aziridine derivative II, where n is 0 or 1, and $R^3$ and $R^4$ are each —COOalk, is carried out, for example, by reacting the starting compound with aqueous or alcoholic ($C_1$-$C_4$-alcohol, preferably methanol) caustic alkali solution (NaOH or KOH) at not more than 120° C., preferably from 40° to 80° C. The resulting hydrazine derivative II, where n is 0 or 1, and $R^3$ and $R^4$ are each H, can be obtained by filtering it off under suction and washing the residue with water, or by extraction from the reaction solution, if necessary after the addition of water, or from the residue after evaporating down the reaction mixture.

The hydrazine derivative, either in aqueous or alcoholic suspension or solution or without prior isolation from the reaction mixture, can be oxidized by the addition of aqueous NaOCl or $H_2O_2$ solution, at not more than 100° C., preferably from 40° to 90° C., to give the azo compound II, wherein n is 0 or 1 and $R^3$ and $R^4$ together constitute a bond. The end product can be isolated from the reaction mixture in a manner similar to that described for the hydrazine derivative.

Depending on the solubility of the alkali metal hydroxide, for example, an aqueous or methanolic solution containing from 1 to 600 g of alkali metal hydroxide per liter of solution is reacted with the compound II, from 4 to 10 moles of alkali metal hydroxide being used per mole of compound II.

For the oxidation, an aqueous sodium hypochlorite or hydrogen peroxide solution containing from 1 to 600 g of the oxidizing agent per liter of solution is used, from 1 to 10 moles, preferably from 1 to 2 moles, of the oxidizing agent being employed per mole of compound II.

The substituents of the $C_1$ bridge can be in the syn or anti position with respect to the four-membered diaza ring. The invention therefore embraces the pure isomers as well as the isomer mixtures.

A group of the novel diazatricyclononene derivatives I is advantageously obtained if a quadricyclane derivative of the formula III

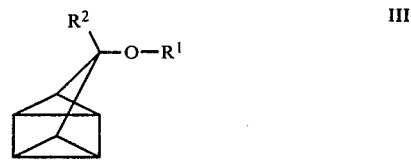

where $R^1$ has the above meanings, is reacted with a dialkyl azodicarboxylate of the formula IV

at not more than 160° C.

The alkyl radicals in IV may be, for example, methyl, ethyl, n-propyl, i-propyl, n-butyl, t-butyl, neopentyl, hexyl, 2-ethylhexyl, nonyl or decyl.

The procedure for obtaining the novel intermediates is described in detail below.

The reaction of the quadricyclane derivative III (J.Amer.Chem.Soc. 90 (1968), 7276 and 96 (1974), 6400) with the dialkyl azodicarboxylate IV which is known from the literature (Houben-Weyl 10/2, 807 et seq.) to give the diazatricyclononene derivative I can be carried out in the presence or absence of a solvent, in general at not more than 160° C., preferably from 20° to 130° C.

To facilitate the removal of the heat of reaction, the reaction is advantageously carried out in a solvent, eg. toluene, xylene, chlorobenzene, petroleum ether, ether, dichloromethane, chloroform, methanol, ethanol or isobutanol, or a mixture of these.

The reaction may, if required, also be carried out under superatmospheric or reduced pressure. The reactants may be employed in stoichiometric amounts, or one of them may be employed in less than the stoichiometric amount or in excess.

The products are isolated by a conventional method, for example by partially or completely distilling off the solvent, and can be purified by extraction or digesting with solvents, recrystallization or distillation under reduced pressure from an oil pump.

The —O—$R^1$ group can be in the syn or anti position with respect to the four-membered diaza ring. These compounds can therefore occur as pure isomers or as mixtures of isomers, as obtained in the preparation, where the compositions of the mixtures vary.

The other group of intermediates I, i.e. the corresponding azo compounds, can be obtained from the above compounds be decarboxylation and oxidation, as described above.

The starting materials can be prepared, for example, by the following methods:

METHOD 1

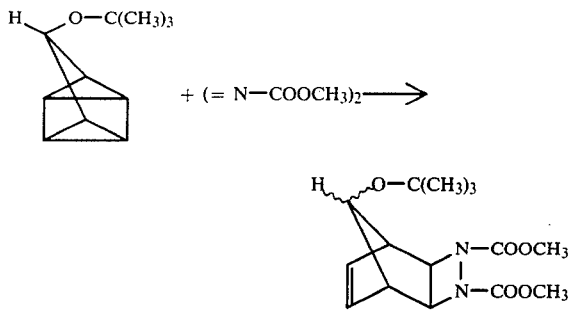

13 parts (parts by weight) of dimethyl azodicarboxylate were added dropwise to 15 parts of 7-t-butoxyquadricyclane and 50 parts of toluene at 80° C., while stirring, and stirring was continued for 12 hours at 80° C. The reaction mixture was evaporated down in a rotary evaporator at from 20° to 50° C. and under 20 mbar, and the residue was then extracted with 200 parts of petroleum ether for 10 hours. The petroleum ether phase was evaporated down and the residue was dried under 20 mbar to give 24 parts (93 mole %) of 3,4-dimethoxycarbonyl-9-t-butoxy-3,4-diazatricyclo[4,2,1,0$^{2,5}$]non-7-ene of melting point 86° C. (toluene/naphtha).

The following compounds were prepared by a similar procedure:

| R$^1$ | R$^3$, R$^4$ | Fp [°C.] |
|---|---|---|
| (CH$_3$)$_3$C— | C$_2$H$_5$— | 33 |
| CH$_3$CO— | CH$_3$— | 176 |
| CH$_3$CO— | C$_2$H$_5$— | 57 |
| CH$_3$CO— | C$_4$H$_9$— | 29 |

METHOD 2

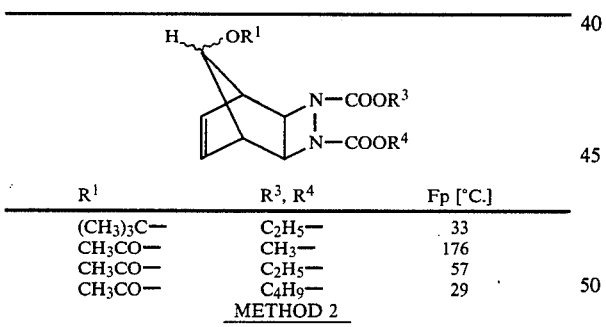

92 parts of 3,4-dimethoxycarbonyl-9-acetoxy-3,4-diazatricyclo[4,2,1,0$^{2,5}$]non-7-ene and 570 parts of 20 percent strength aqueous NaOH were stirred for 3 hours at 70° C., after which 356 parts of 13 percent strength by weight aqueous NaOCl were added dropwise at 40° C. and stirring was continued for 1 hour at 40° C. The reaction mixture was extracted continuously for 12 hours with 300 parts of CH$_2$Cl$_2$, the organic phase was dried with MgSO$_4$, treated with active charcoal and evaporated down, and the residue was digested with 200 parts of petroleum ether. 36.4 parts (86 mol %) of 9-hydroxy-3,4-diazatricyclo[4,2,1,0$^{2,5}$]nona-3,7-diene of melting point 128° C. (from cyclohexane) were obtained.

METHOD 3

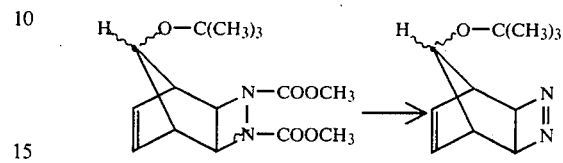

50 parts of 3,4-dimethoxycarbonyl-9-t-butoxy-3,4-diazatricyclo[4,2,1,0$^{2,5}$]non-7-ene, 50 parts of KOH and 250 parts of methanol were refluxed for 7 hours, after which 36 parts of 30 percent strength aqueous H$_2$O$_2$ were added dropwise at 60° C. and stirring was continued for a further hour at 60° C. The mixture was cooled to 20° C., and thereafter the solid product was filtered off under suction and washed with 50 parts of methanol, the combined filtrates were evaporated down in a rotary evaporator at from 20° to 40° C. and under 20 mbar, and the residue was extracted in a soxhlet for 12 hours with 300 parts of petroleum ether. The petroleum ether phase was evaporated down to give 28.5 parts (93 mole %) of 9-t-butoxy-3,4-diazatricyclo[4,2,1,0$^{2,5}$]nona-3,7-diene of melting point 78° C. (from naphtha).

METHOD 4

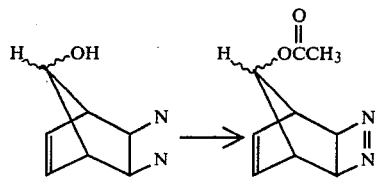

5 parts of 9-hydroxy-3,4-diazatricyclo[4,2,1,0$^{2,5}$]nona-3,7-diene, 5 parts of acetic anhydride, 1 part of triethylamine and 100 parts of ether were refluxed for 24 hours, after which the reaction mixture was extracted twice with 50 parts of water, and the organic phase was dried with MgSO$_4$ and evaporated down in a rotary evaporator to give 6.2 parts (95 mole %) of 9-acetoxy-3,4-diazatricyclo[4,2,1,0$^{2,5}$]nona-3,7-diene of melting point 58° C.

The following compounds were prepared by a similar procedure:

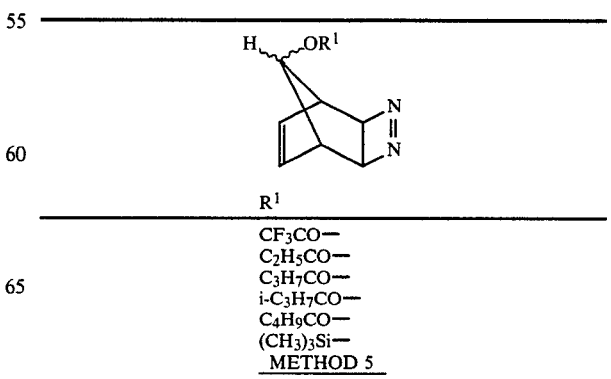

R$^1$

CF$_3$CO—
C$_2$H$_5$CO—
C$_3$H$_7$CO—
i-C$_3$H$_7$CO—
C$_4$H$_9$CO—
(CH$_3$)$_3$Si—

METHOD 5

-continued

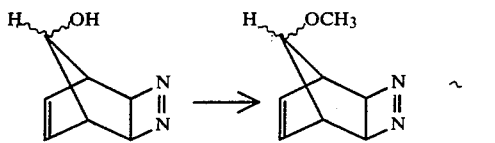

1 part of NaH was added, a little at a time, to 5 parts of 9-hydroxy-3,4-diazatricyclo[4,2,1,0$^{2,5}$]nona-3,7-diene and 100 parts of acetonitrile at 20° C., while stirring. Thereafter, 20 parts of methyl iodide were added and stirring was continued for 12 hours at 20° C. The reaction mixture was evaporated down in a rotary evaporator at from 20° to 50° C. and under 20 mbar, and the residue was extracted with 200 parts of petroleum ether. The petroleum ether phase was evaporated down to give 5 parts (90 mole %) of 9-methoxy-3,4-diazatricyclo[4,2,1,0$^{2,5}$]-nona-3,7-diene as an oil. $^1$H-NMR ($\delta$ in ppm): 6.2 (bs, 2H), 4.1 (bs, 2H), 3.1–3.3 (m, 6H).

The following compounds were prepared by a similar procedure:

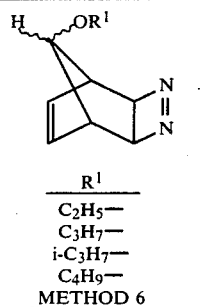

| R$^1$ |
|---|
| C$_2$H$_5$— |
| C$_3$H$_7$— |
| i-C$_3$H$_7$— |
| C$_4$H$_9$— |

METHOD 6

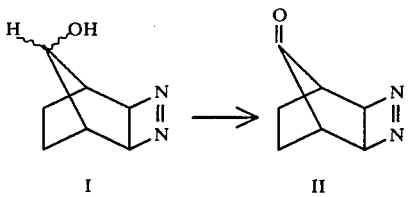

1.3 parts of orthophosphoric acid were added, a little at a time, to a mixture of 18.5 parts of I, 78 parts of dicyclohexylcarbodiimide and 140 parts of anhydrous dimethylsulfoxide at from 20° to 30° C., while stirring and cooling, and stirring was continued for 5 hours at about 25° C. 460 parts of CH$_2$Cl$_2$ were added, after which the mixture was filtered and the filtrate was stirred with 400 parts of saturated aqueous NaHCO$_3$ solution and 10 parts of sodium carbonate for 3 hours at 25° C. The organic phase was separated off, the aqueous phase was extracted 5 times with 200 parts of CH$_2$Cl$_2$, the combined organic phases were washed twice with 300 parts of water, dried with MgSO$_4$ and treated with active charcoal and then evaporated down, and the residue was extracted continuously with 200 parts of petroleum ether for 12 hours. The petroleum ether phase was evaporated down to give 14.5 parts (79 mole %) of II of melting point 90° C.

The novel compounds of the formula I can, for example, be prepared similarly to the Examples below.

EXAMPLE 1

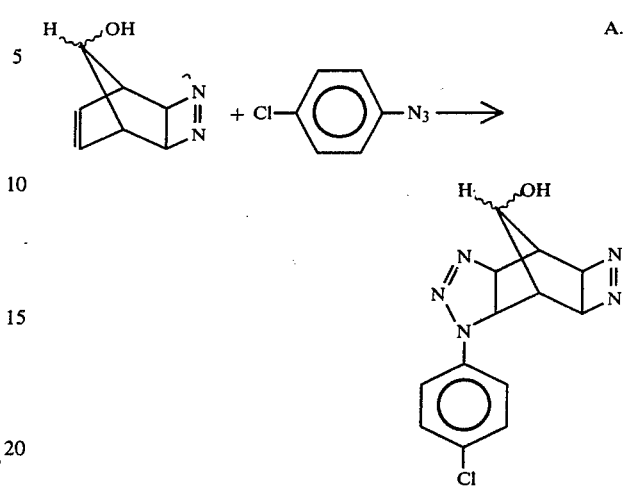

30 parts of 9-hydroxy-3,4-diazatricyclo[4,2,1,0$^{2,5}$]-nona-3,7-diene and 34 parts of p-chlorophenyl azide in 100 parts of toluene were heated at 80° C. for 3 hours, while stirring. The mixture was evaporated down in a rotary evaporator at from 20° to 40° C. and under 20 mbar, after which the residue was digested successively with 100 parts of diethyl ether and 100 parts of petroleum ether, and the product was dried at 20° C. under 1 mbar. 59 parts (92 mole %) of 8-(4-chlorophenyl)-12-hydroxy-3,4,8,9,10-pentazatetracyclo[5,4,1,0$^{2,5}$,0$^{7,11}$]dodeca-3,9-diene of melting point 178° C. (decomposition) were obtained (Command No. 1).

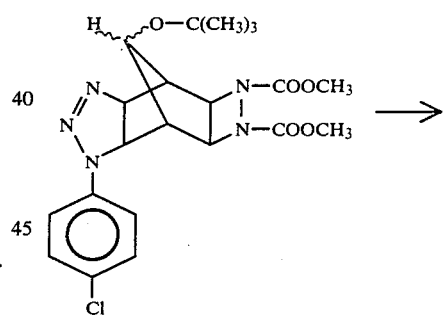

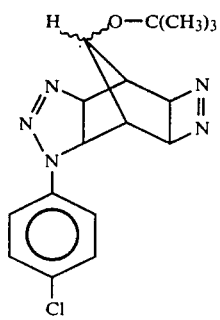

400 parts of 3,4-dimethoxycarbonyl-8-(4-chlorophenyl)-12-t-butoxy-3,4,8,9,10-pentazatetracyclo[5,4,1,0$^{2,5}$,0$^{7,11}$]dodec-9-ene (Compound No. 9) were suspended in 1,000 parts of 25 percent strength aqueous sodium hydroxide solution, and the suspension was stirred for 6 hours at 85° C. Thereafter, 1,150 parts of 13 percent strength aqueous NaOCl were added at 60° C. in the course of 2 hours, and stirring was continued for 4 hours at 60° C. The mixture was cooled to 20° C., after which the solid product was filtered off under suction, washed with 3,000 parts of water and dried at 30° C. under 1 mbar. 270 parts (96 mole %) of 8-(4-chlorophenyl)-12-t-butoxy-3,4,8,9,10-pentazatetracyclo[5,4,1,0$^{2,5}$,0$^{7,11}$]dodeca-3,9-diene of melting point 178° C. (decomposition) were obtained (Compound No. 2).

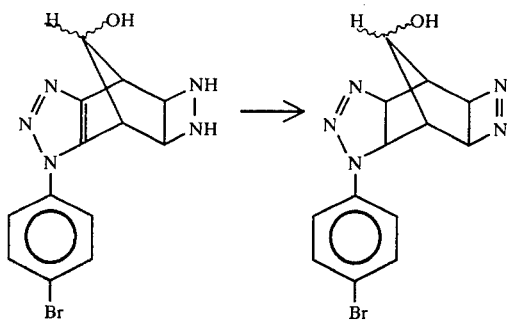

35 parts of 30 percent strength aqueous H$_2$O$_2$ were added dropwise, in the course of 1 hour, to 50 parts of 8-(4-bromophenyl)-12-hydroxy-3,4,8,9,10-pentazatetracyclo[5,4,1,0$^{2,5}$,0$^{7,11}$]dodec-9ene (Compound No. 69) in 400 parts of methanol and 5 parts of 25 percent strength by weight aqueous NaOH, at 65° C., while stirring, and stirring was continued for 5 hours at 65° C. The mixture was cooled to 20° C., after which 1,500 parts of water were added, and the product was filtered off under suction, washed with 300 parts of water and dried at 30° C. under 1 mbar. 44 parts (88 mole %) of 8-(4-bromophenyl)-12hydroxy-3,4,8,9,10-pentazatetracyclo[5,4,1,0$^{2,5}$,0$^{7,11}$]-dodeca-3,9-diene of melting point 187° C. (decomposition) were obtained (Compound No. 3).

The following compounds were prepared similarly:

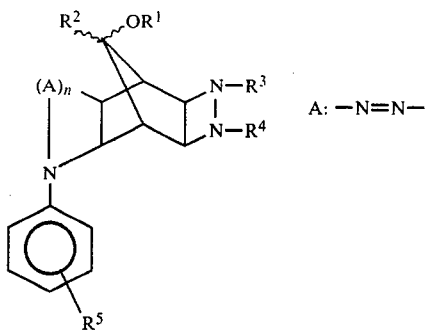

Where R$^1$ and R$^2$ constitute a bond, the molecule contains the following radical in the 12-position:

| Compound No. | R$^1$ | R$^2$ | R$^3$ | R$^4$ | R$^5$ | n | Mp. [°C.] |
|---|---|---|---|---|---|---|---|
| 4 | H— | H— | a bond | | H— | 1 | 148 (decomposition) |
| 5 | " | " | " | | m-CF$_3$— | 1 | 177 (decomposition) |
| 6 | " | " | " | | p-F— | 1 | 181 (decomposition) |
| 7 | " | " | " | | o-Br— | 1 | 166 (decomposition) |
| 8 | " | " | " | | m-CF$_3$— | 0 | 135 (decomposition) |
| 9 | (CH$_3$)$_3$C— | " | CH$_3$OCO— | CH$_3$OCO— | o-Cl— | 1 | 186 (decomposition) |
| 10 | " | " | " | " | m-CF$_3$— | 1 | 183 (decomposition) |
| 11 | " | " | " | " | p-Br— | 1 | 210 (decomposition) |
| 12 | " | " | C$_2$H$_5$OCO— | C$_2$H$_5$OCO— | H— | 1 | 184 (decomposition) |
| 13 | " | " | " | " | p-Br— | 1 | 179 (decomposition) |
| 14 | " | " | a bond | | m-CF$_3$— | 1 | 192 (decomposition) |
| 15 | (CH$_3$)$_3$C— | H— | " | | p-Br— | 1 | 200 (decomposition) |
| 16 | " | " | " | | p-Br— | 0 | 133 (decomposition) |
| 17 | a bond | | " | | m-CF$_3$— | 1 | 168 (decomposition) |
| 18 | " | | " | | p-Cl— | 1 | 186 (decomposition) |
| 19 | " | | " | | m-Cl— | 1 | 173 (decomposition) |
| 20 | " | | " | | p-Br— | 1 | 187 (decomposition) |
| 21 | " | | " | | m-CF$_3$— | 0 | 138 (decomposition) |
| 22 | " | | " | | p-Cl— | 0 | 151 (decomposition) |
| 23 | CF$_3$CO— | H— | " | | p-Cl— | 1 | 180 (decomposition) |
| 24 | " | " | " | | m-CF$_3$— | 1 | 177 (decomposition) |
| 25 | CH$_3$CO— | " | CH$_3$OCO— | CH$_3$OCO— | p-Cl— | 1 | 197 (decomposition) |
| 26 | " | " | " | " | o-Cl— | 1 | 174 (decomposition) |
| 27 | " | " | " | " | m-CF$_3$— | 1 | 175 (decomposition) |
| 28 | " | " | " | " | p-Br— | 1 | 153 (decomposition) |
| 29 | " | " | C$_4$H$_9$OCO— | C$_4$H$_9$OCO— | H— | 1 | 191 (decomposition) |
| 30 | " | " | " | " | p-Cl— | 1 | 182 (decomposition) |
| 31 | " | " | " | " | p-F— | 1 | 180 (decomposition) |
| 32 | CH$_3$CO | H | a bond | | p-Cl— | 1 | 185 (decomposition) |
| 33 | " | " | " | | m-CF$_3$— | 1 | 152 (decomposition) |
| 34 | " | " | " | | m-Br— | 1 | 187 (decomposition) |
| 35 | " | " | " | | p-Br— | 1 | 193 (decomposition) |
| 36 | CH$_3$— | " | " | | p-Br— | 0 | 139 (decomposition) |
| 37 | " | " | " | | m-CF$_3$— | 1 | 176 (decomposition) |
| 38 | " | " | " | | p-Br— | 1 | 191 (decomposition) |
| 39 | " | " | " | | p-Cl— | 1 | 183 (decomposition) |
| 40 | " | " | " | | p-Cl— | 0 | 138 (decomposition) |
| 41 | C$_2$H$_5$— | " | " | | H— | 1 | 178 (decomposition) |
| 42 | " | " | " | | p-Cl— | 1 | 179 (decomposition) |

-continued

| Compound No. | R¹ | R² | R³ | R⁴ | R⁵ | n | Mp. [°C.] |
|---|---|---|---|---|---|---|---|
| 43 | " | " | | " | p-F— | 1 | 174 (decomposition) |
| 44 | " | " | | " | p-Br— | 0 | 133 (decomposition) |
| 45 | C₂H₅CO— | " | | " | p-Cl— | 1 | 189 (decomposition) |
| 46 | " | " | | " | m-CF₃— | 1 | 185 (decomposition) |
| 47 | CH₃CH(CH₃)CO— | H— | | " | p-Br— | 1 | 149 (decomposition) |
| 77 | (CH₃)₃Si— | " | | " | p-Cl— | 1 | 186 (decomposition) |
| 78 | " | " | | " | m-CF₃— | 1 | 189 (decomposition) |
| 79 | " | " | | " | p-Br— | 1 | 178 (decomposition) |

EXAMPLE 2

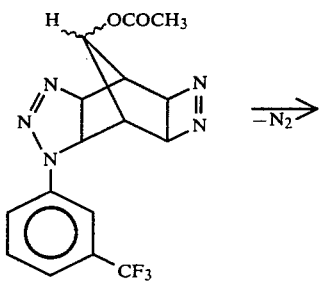

$\xrightarrow{-N_2}$

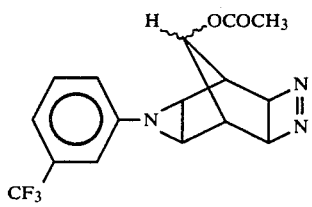

10 parts of 8-(3-trifluoromethylphenyl)-12-acetoxy-3,4,8,9,10-pentazatetracyclo[5,4,1,0$^{2,5}$,0$^{7,11}$]dodeca-3,9-diene (Compound No. 33) in 50 parts of acetic acid and 150 parts of ether were stirred for 5 hours at 25° C. The mixture was evaporated down in a rotary evaporator at 20° C. under from 1 to 20 mbar, after which the residue was digested successively with 50 parts of ether and 50 parts of petroleum ether. The product was dried, and 9.1 parts (94 mole %) of 8-(3-trifluoromethylphenyl)-12-acetoxy-3,4,8-triazatetracyclo[4,3,1,0$^{2,5}$,0$^{7,9}$]dec-3-ene of melting point 154° C. (decomposition) were obtained (Compound No. 48).

The following compounds were prepared by a similar procedure:

| Compound No. | R¹ | R² | R³ | R⁴ | R⁵ | Mp. [°C.] |
|---|---|---|---|---|---|---|
| 49 | H— | H— | a bond | | H— | 132 (decomposition) |
| 50 | " | " | " | | p-Cl— | 124 (decomposition) |
| 51 | " | " | " | | p-Br— | 141 (decomposition) |
| 52 | (CH₃)₃C— | " | CH₃OCO— | CH₃OCO— | m-CF₃— | 98 (decomposition) |
| 53 | " | " | " | " | p-Cl— | 74 (decomposition) |
| 54 | " | " | C₂H₅OCO— | C₂H₅OCO— | p-Br— | 60 (decomposition) |
| 55 | " | " | a bond | | p-Cl— | 149 (decomposition) |
| 56 | " | " | " | | m-CF₃— | 121 (decomposition) |
| 57 | a bond | | " | | p-Br— | 129 (decomposition) |
| 58 | CF₃CO— | H— | " | | p-Cl— | 82 |
| 59 | CH₃CO— | " | CH₃OCO— | CH₃OCO— | p-Cl— | 87 |
| 60 | " | " | " | " | m-CF₃— | 61 |
| 61 | " | " | " | " | p-Br— | 64 |
| 62 | " | " | a bond | | p-Cl— | 126 (decomposition) |
| 63 | CH₃— | " | " | | m-CF₃— | 131 (decomposition) |
| 64 | " | " | " | | p-Br— | 144 (decomposition) |
| 65 | C₂H₅— | " | " | | m-CF₃— | 128 (decomposition) |
| 80 | (CH₃)₃Si— | " | " | | p-Cl— | 150 (decomposition) |
| 81 | " | " | " | | m-CF₃— | 128 (decomposition) |

EXAMPLE 3

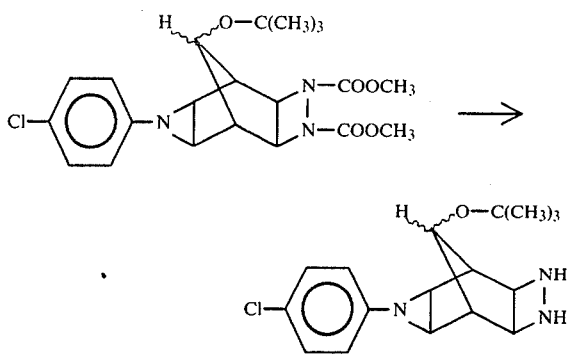

300 parts of 3,4-dimethoxycarbonyl-8-(4-chlorophenyl)-12-t-butoxy-3,4,8-triazatetracyclo[4,3,1,0$^{2,5}$,0$^{7,9}$]decane (Compound No. 53), 150 parts of NaOH and 2,000 parts of methanol were heated for 6 hours at 65° C., while stirring. Thereafter, the mixture was filtered under suction, the residue was washed with 500 parts of methanol and the filtrate was evaporated down in a rotary evaporator at from 20° to 40° C. under 20 mbar. The residue was washed with 1,000 parts of water and dried at from 20° to 40° C. under 1 mbar. 185 parts (84 mole %) of 8-(4-chlorophenyl)-12-t-butoxy-3,4,8-triazatetracyclo[4,3,1,0$^{2,5}$,0$^{7,9}$]decane of melting point 89° C. were obtained (Compound No. 66).

The following compounds were obtained by a similar procedure:

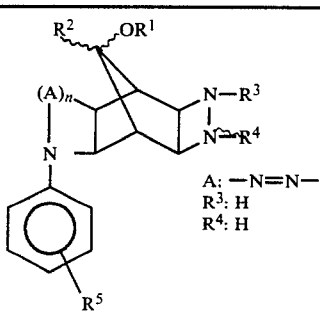

A: —N=N—
R$^3$: H
R$^4$: H

| Compound No. | R$^1$ | R$^2$ | R$^5$ | n | Mp. [°C.] |
|---|---|---|---|---|---|
| 67 | H— | H— | H— | 1 | 123 (decomposition) |
| 68 | H— | H— | p-Cl— | 1 | 142 (decomposition) |
| 69 | H— | H— | p-Br— | 1 | 137 (decomposition) |
| 70 | H— | H— | m-CF$_3$— | 1 | 150 (decomposition) |
| 71 | H— | H— | p-Cl— | 0 | 83 |
| 72 | H— | H— | m-CF$_3$— | 0 | 41 |
| 73 | (CH$_3$)$_3$C— | H— | p-Cl— | 1 | 139 (decomposition) |
| 74 | " | H— | m-CF$_3$— | 1 | 148 (decomposition) |
| 75 | " | H— | p-Br— | 1 | 160 (decomposition) |
| 76 | " | H— | m-CF$_3$— | 0 | 74 |

The new active ingredients according to the invention influence plant metabolism, and may therefore be used as plant growth regulators.

Experience has shown that plant growth regulators may have either one or several different effects on plants.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation of the active ingredient; and
(g) the concentration at which the active ingredient is applied.

At all events, plant growth regulators have a positive and desired effect on crop plants.

A description of some of the various possibilities of using the growth regulators according to the invention in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

A further mechanism for increasing yields with growth regulators is based on the fact the the nutrients are employed to a greater extent for blossom and fruit formation, whereas vegetative growth is restricted. Because the leaf or plant mass is relatively low, this also counteracts attack by various, particularly fungal, diseases.

The inhibition of vegetative growth also makes closer planting possible in numerous crops, which means an increase in yield based on the area cropped. The compounds according to the invention are particularly suitable for suppressing vegetative growth in crop plants such as soybeans, sunflowers, groundnuts, rape, ornamentals, cotton, rice and grasses.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for readily controllable defoliation of plants.

The action of the compounds according to the invention is superior to that of prior art growth regulators. This action is manifested not only in monocotyledon crops, e.g., cereals such as wheat, barley, rye, oats and rice or Indian corn or grasses, but also particularly in dicotyledons (e.g., sunflowers, tomatoes, groundnuts, grapes, cotton, rape and, particularly, soybeans) and various ornamentals such as chrysanthemums, poinsettias and hibiscus.

The compounds according to the invention may be applied to the crop either by treating the seed, treating the soil, i.e., through the roots, or—the method particularly preferred—by spraying the leaves.

Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.001 to 12 kg/ha, preferably from 0.01 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, ketones, e.g. cyclohexanone, dimethylformamide, and water; solid carriers, for example natural rock powders, e.g. kaolin, alumina, talc and chalk, and synthetic rock powders, e.g. highly disperse silica and silicates; emulsifiers, and other surfactants, for example non-ionic and anionic emulsifiers, e.g polyoxyethylene fatty alcohol ethers and alkylsulfonates, and dispersants, for example lignin, sulfite waste liquors and methylcellulose. It is preferred to use the compounds according to the invention in aqueous solution, if desired with the addition of water-miscible organic solvents such as methanol or other lower alcohols, acetone, dimethylformamide or N-methylpyrrolidone. The formulations in general contain from 0.1 to 95% by weight of active ingredient, preferably from 0.5 to 90%.

The formulations, and the ready-to-use preparations obtained therefrom, e.g. solutions, emulsions, suspensions, powders, dusts, pastes or granules, are applied in the conventional manner, e.g., preemergence, postemergence, or as seed disinfectants.

The agents according to the invention many, in these application forms, also be mixed and applied with other active ingredients, e.g., herbicides, insecticides, other growth regulators, fungicides and fertilizers. When mixed with other growth regulators, the spectrum of action is in many cases increased; with a number of these compositions, synergistic effects also occur; i.e., the action of the combination product is greater than the effect of the individual components added together.

The following examples demonstrate the action of the compounds to be used in accordance with the invention as growth regulators; however, further applications as growth regulators are not excluded.

Comparative compounds

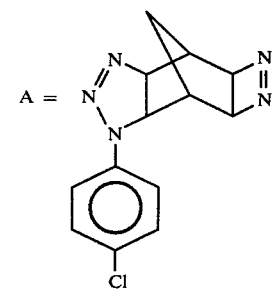

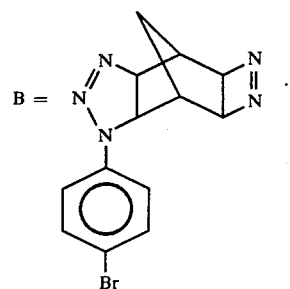

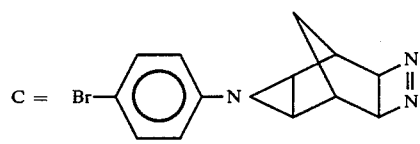

Experiment

Growth-regulating action

To determine the growth-regulating properties of the candidate compounds, soil provided with sufficient nutrients was filled into plastic pots about 12.5 cm in diameter and test plants were grown therein.

For the preemergence treatment, the candidate compounds were poured, as aqueous formulations, onto the seedbed on the day of sowing.

For the postemergence treatment, the compounds were sprayed onto the plants. The growth-regulating action observed was confirmed at the end of the experiment by height measurements. The values obtained were compared with those for untreated plants.

Not only was growth height reduced—the leaves also took on a more intense color. The increased chlorophyll content is indicative of a higher rate of photosynthesis, making for bigger yields.

In this experiment, active ingredients 39 and 77 reduced growth height in spring barley, on preemergence application of 3 and 12 mg per vessel, to a much greater extent than compounds A, B and C.

In a further experiment, active ingredients 1, 3, 32 and 48 reduced growth in lawns, on postemergence application of 1.5 and 6 mg per vessel, to a much greater extent than compounds A, B and C.

EXAMPLE I 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

EXAMPLE II 3 parts by weight of compound 3 is intimately mixed with 97 parts by weight of particulate kaolin. A dust is obtained containing 3% by weight of the active ingredient.

EXAMPLE III 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE IV 40 parts by weight of compound 3 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

EXAMPLE V 20 parts of compound 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained.

EXAMPLE VI 20 parts by weight of compound 39 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

EXAMPLE VII 80 parts by weight of compound 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By finely distributing the mixture in water, a spray liquor is obtained.

The active ingredients may also be successfully used in the ultra-low-volume method, where formulations containing more than 95 wt% of active ingredient, or even the active ingredient without any additives at all, are applied.

We claim:

1. A norbornane compound of the formula

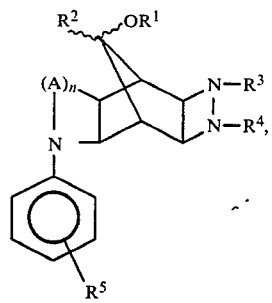

where A is —N=N—, n is 0 or 1, $R^1$ is hydrogen, trimethylsilyl or trifluoroacetyl, or an acyclic or cyclic alkyl or alkylcarbonyl radical wherein each of the alkyl substituents contain from 1 to 5 carbon atoms, or $R^1$ and $R^2$ together constitute a bond, the steric arrangement of substituents $OR^1$ and $R^2$ at the $C_1$ bridge not being defined, and $R^3$ and $R^4$ are independently hydrogen or a $C_1$–$C_4$ alkyoxycarbonyl, or together constitute a bond, and $R^5$ is hydrogen, a halogen or $C_1$–$C_4$ haloalkyl wherein in each instance the halogen substituent is selected from the group consisting of fluorine, bromine and chlorine.

2. An agent for regulating plant growth, containing a compound as claimed in claim 1.

3. A process for regulating plant growth, wherein the plants, the soil or the seed of the plants are treated with a compound as claimed in claim 1.

* * * * *